(12) United States Patent
Liu

(10) Patent No.: US 9,901,099 B1
(45) Date of Patent: Feb. 27, 2018

(54) METHOD FOR MANUFACTURING NATURAL PESTICIDE AND WATER QUENCHING DEVICE THEREFORE

(71) Applicant: DE-DA B&C PRO CO., LTD., Taoyuan (TW)

(72) Inventor: Chun-Yung Liu, Taoyuan (TW)

(73) Assignee: DE-DA B&C PRO CO., LTD., Taoyuan (TW)

( * ) Notice: Subject to any disclaimer, the term of this patent is extended or adjusted under 35 U.S.C. 154(b) by 18 days.

(21) Appl. No.: 15/342,208

(22) Filed: Nov. 3, 2016

(51) Int. Cl.
| | |
|---|---|
| *B01D 5/00* | (2006.01) |
| *A01N 59/00* | (2006.01) |
| *C10B 39/04* | (2006.01) |
| *C10B 53/02* | (2006.01) |
| *C05F 11/08* | (2006.01) |

(52) U.S. Cl.
CPC .............. *A01N 59/00* (2013.01); *B01D 5/006* (2013.01); *B01D 5/0027* (2013.01); *B01D 5/0072* (2013.01); *C05F 11/08* (2013.01); *C10B 39/04* (2013.01); *C10B 53/02* (2013.01)

(58) Field of Classification Search
CPC ......... C10B 39/04; C10B 53/02; A01N 59/00; C05F 11/08; B01D 5/0027; B01D 5/006; B01D 5/0072; B01D 1/26
See application file for complete search history.

(56) References Cited

U.S. PATENT DOCUMENTS

| | | | | | |
|---|---|---|---|---|---|
| 2,758,031 | A | * | 8/1956 | Ozai-Durrani | A23L 7/196 426/461 |
| 3,408,202 | A | * | 10/1968 | Serbia | A23L 7/196 426/450 |
| 4,107,226 | A | * | 8/1978 | Ennis, Jr. | C10G 9/002 208/130 |
| 5,547,548 | A | * | 8/1996 | Siddoway | C10B 39/04 201/28 |
| 2016/0264871 | A1 | * | 9/2016 | Honjo | C10B 39/04 |

* cited by examiner

*Primary Examiner* — Jonathan Miller
(74) *Attorney, Agent, or Firm* — Jackson IPG PLLC

(57) ABSTRACT

A method for manufacturing a natural pesticide and a water quenching device thereof are provided. The method includes the steps of: burning paddy at a high temperature of 400-900° C. into carbonized paddy, wherein the carbonized paddy comprises at least 50% silica, at least 10% organic matter, at least 2% potassium, and at most 2% water; using a water quenching device to quench and heat the carbonized paddy, enabling the carbonized paddy to form a gas and a solid substance by means of solid-liquid separation; using the water quenching device to condense the gas separated from the carbonized paddy into a liquid; and testing a PH value of the liquid after condensation through the water quenching device, wherein when the PH value of the liquid is alkaline, the liquid is outputted and stored as a pesticide.

11 Claims, 4 Drawing Sheets

METHOD FOR MANUFACTURING NATURAL PESTICIDE AND WATER QUENCHING DEVICE THEREFORE

FIELD OF THE INVENTION

The present invention relates to a method for manufacturing a natural pesticide or bactericide and a water quenching device thereof.

BACKGROUND OF THE INVENTION

A pesticide is a substance used for killing pets, which is often applied to agriculture, medicine, industry and home environment. In general, pesticides can be systemic or contact. The systemic pesticide is in corporation with plants. When pests eat plants, they also absorb pesticides. The contact pesticide is absorbed directly when pests are in contact with plants.

As to the hazards of pests to the growth and storage of crops, the crop yield may decrease greatly. As a result, the cost is increased to consumers. In order to achieve a high efficiency of crop productions, it is quite important for a pest control. Most pesticides are made of chemical materials. When the pesticide is applied to plants, it will permeate into the soil and into the plants from the roots to kill pests through the neurotoxin of the pesticide. However, most pests may be resistance to pesticides after a period of time. Thus, it is necessary to increase the dosage of the pesticide for plants. This not only causes soil acidification but also make the plants remain chemicals to influence the human health.

SUMMARY OF THE INVENTION

In view of the problems of the prior art, the primary object of the present invention is to provide a method for manufacturing a natural pesticide or bactericide and a water quenching device thereof to reduce the hazards to the environment and the human body.

According to one aspect of the present invention, a method for manufacturing a natural pesticide is provided. The method comprises the steps of: burning paddy at a high temperature of 400-900° C. into carbonized paddy, wherein the carbonized paddy comprises at least 50% silica, at least 10% organic matter, at least 2% potassium, and at most 2% water; using a water quenching device to quench and heat the carbonized paddy, enabling the carbonized paddy to form a gas and a solid substance by means of solid-liquid separation; using the water quenching device to condense the gas separated from the carbonized paddy into a liquid; and testing a PH value of the liquid after condensation through the water quenching device, wherein when the PH value of the liquid is alkaline, the liquid is outputted and stored as a pesticide.

Preferably, the method for manufacturing a natural pesticide further comprises the step of: using the water quenching device to collect the solid substance separated from the carbonized paddy by means of gas separation, wherein the solid substance is heated and crushed to form a small substance, and the small substance is added with *trichoderma* to form an organic fertilizer.

Preferably, the small substance is added with *actinomyces*.

Preferably, the small substance is added with *bacillus*.

According to another aspect of the present invention, a water quenching device for manufacturing a natural pesticide is provided. The water quenching device comprises: a first water quenching and heating area for inputting carbonized paddy and quenching and heating the carbonized paddy, enabling the carbonized paddy to form a gas and a solid substance by means of solid-liquid separation, wherein the carbonized paddy is formed by burning paddy at a high temperature of 400-900° C. and the carbonized paddy comprises at least 50% silica, at least 10% organic matter, at least 2% potassium, and at most 2% water; a first condenser connected with the first water quenching and heating area and configured to condense the gas separated from the carbonized paddy into a liquid; and at least one second water quenching and heating area connected with the first condenser to receive the liquid which is condensed from the gas by the first condenser and to perform a PH value test, wherein when the PH value of the liquid is alkaline, the liquid is outputted and stored as a pesticide.

Preferably, the at least one second water quenching and heating area is plural. A second condenser is connected between every two of the second water quenching and heating areas. When the second water quenching and heating area connected with the first condenser tests and determines that the liquid doesn't reach an alkaline standard, the liquid is heated again by the second water quenching and heating area and changed into a gas. The gas is condensed by the second condenser, and the liquid after condensation is delivered to the next one of the second water quenching and heating areas to give a PH value test.

Preferably, the first water quenching and heating area and the second water quenching and heating area comprise a tank body and a heater, respectively.

Preferably, the second water quenching and heating area further comprises a PH value detector, and the PH value detector is electrically connected with the heater.

Preferably, the first water quenching and heating area further comprises a collection trough. The collection trough is connected with the tank body for collecting and storing the solid substance separated from the carbonized paddy by means of gas separation, Preferably, the first water quenching and heating area further comprises a delivery member. The delivery member is connected with the tank body for delivering the carbonized paddy to the tank body and delivering the solid substance formed in the tank body to the collection trough.

Preferably, the solid substance is heated and crushed to form a small substance. The small substance is added with *trichoderma, actinomyces, bacillus* or a combination thereof to form an organic fertilizer.

Preferably, an input end of the first condenser is provided with a filter screen.

Preferably, an output end of the first condenser is provided with a gate.

DESCRIPTION OF THE PREFERRED EMBODIMENTS

Figure 1:
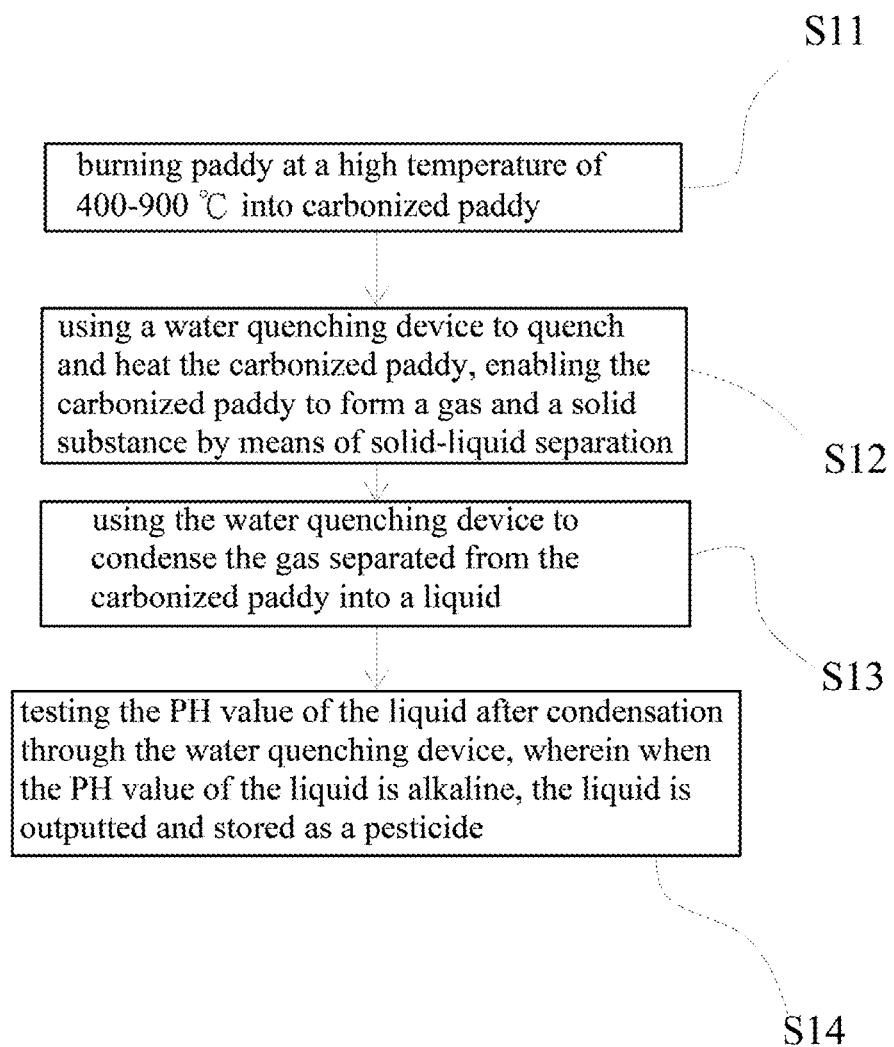
FIG. 1 is a first flow chart of a method for manufacturing a natural pesticide of the present invention.

Advantages and features of the inventive concept and methods of accomplishing the same may be understood more readily by reference to the following detailed description of embodiments and the accompanying drawings. The inventive concept may, however, be embodied in many different forms and should not be construed as being limited to the embodiments set forth herein. In the drawings, the relative sizes of elements should not be construed as being limited to the proportion and arrangement relationship as shown in the drawings and may be exaggerated for clarity, without departing from the spirit and scope of the present invention.

FIG. 1 is a first flow chart of a method for manufacturing a natural pesticide of the present invention. The method comprises the following steps of:

Step S11: burning paddy at a high temperature of 400-900° C. into carbonized paddy, wherein the carbonized paddy comprises at least 50% silica, at least 10% organic matter, at least 2% potassium, and at most 2% water;

Step S12: using a water quenching device to quench and heat the carbonized paddy, enabling the carbonized paddy to form a gas and a solid substance by means of solid-liquid separation;

Step S13: using the water quenching device to condense the gas separated from the carbonized paddy into a liquid;

Step S14: testing the PH value of the condensed liquid through the water quenching device, wherein when the PH value of the liquid is alkaline, the liquid is outputted and stored as a pesticide or a bactericide, wherein when the PH value of the liquid doesn't reach the alkaline standard, the procedures of water quenching, heating and condensing are performed again until meeting the testing standard.

Figure 2:
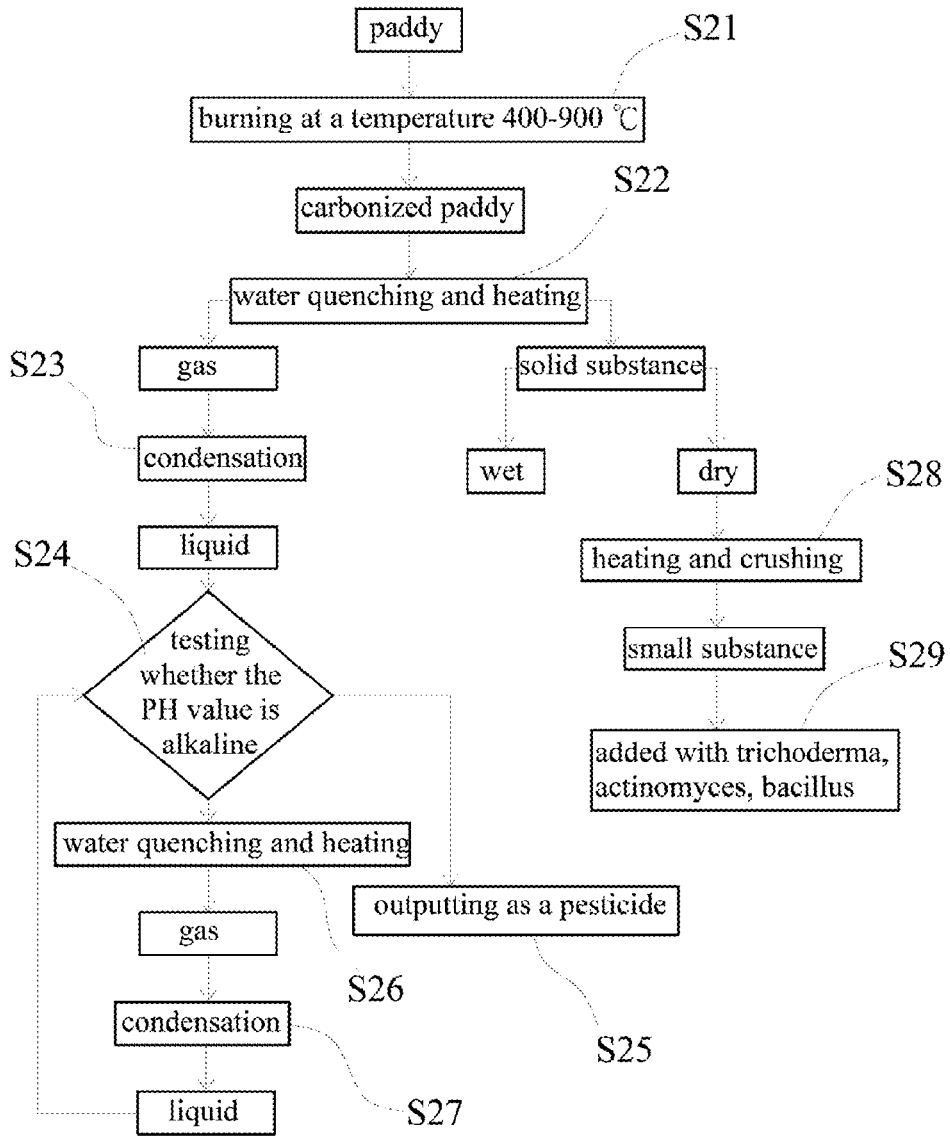
FIG. 2 is a second flow chart of a method for manufacturing a natural pesticide of the present invention.

FIG. 2 is a second flow chart of a method for manufacturing a natural pesticide of the present invention. The present invention uses paddy as the raw material of a pesticide or the raw material a bactericide. First, the paddy is burned at a high temperature of 400-900° C. into carbonized paddy, namely, Step S21; next, perform Step S22, the carbonized paddy is quenched and heated, enabling the carbonized paddy to form a gas and a solid substance by means of solid-liquid separation; furthermore perform Step S23, the gas is condensed to form a liquid by means of condensation; next, the PH value of the liquid is tested through a PH detector to determine whether the liquid reaches the alkaline standard, namely, Step S24; when the PH value of the liquid doesn't reach the alkaline standard, Step S26 is performed, the liquid is quenched and heated again for evaporating the liquid to form a gas; and perform Step S27, the gas is condensed again to form a liquid, and perform the test of the PH value of the liquid; when the liquid becomes alkaline, the liquid is outputted and stored, because the liquid contains silicon, it can be used as a natural pesticide or bactericide, or cleanser, namely, Step S25. The solid substance formed by quenching and heating the carbonized paddy is collected and stored. The solid substance may be divided into two parts, a wet solid substance and a dry solid substance. For the dry solid substance, perform Step S28, the dry solid substance is heated and crushed to form a small substance. The small substance is added with *trichoderma, actinomyces, bacillus* or a combination thereof, namely, Step S29, enabling the small substance to be used as a compound organic fertilizer.

Figure 3:
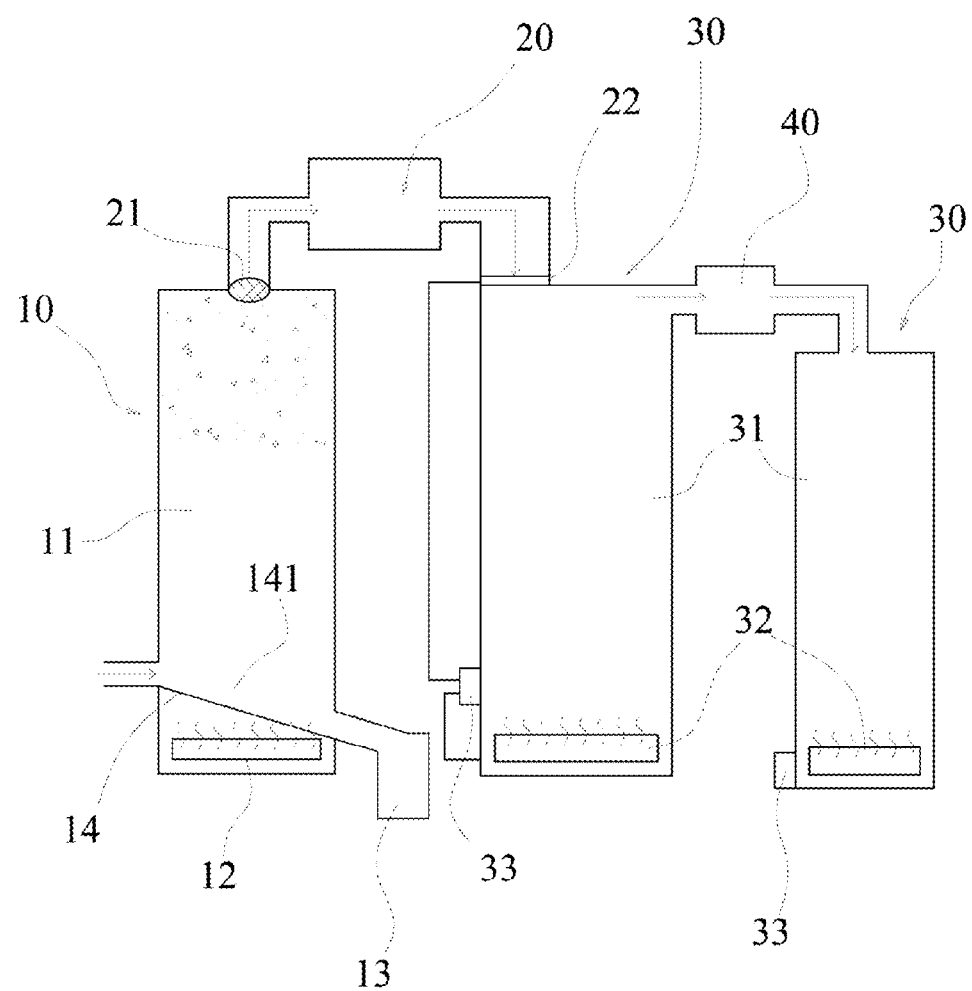
FIG. 3 is a schematic view of a water quenching device for manufacturing a natural pesticide of the present invention.

FIG. 3 is a schematic view of a water quenching device for manufacturing a natural pesticide of the present invention. The water quenching device is used to perform the aforesaid method. The water quenching device comprises a first water quenching and heating area 10, a first condenser 20, and at least one second water quenching and heating area 30.

The first water quenching and heating area 10 is configured to input the carbonized paddy and to quench and heat the carbonized paddy, enabling the carbonized paddy to form a gas and a solid substance by means of solid-liquid separation. Wherein, the carbonized paddy is formed by burning paddy at a high temperature of 400-900° C. The carbonized paddy comprises at least 50% silica, at least 10% organic matter, at least 2% potassium, and at most 2% water. Furthermore, the first water quenching and heating area 10 comprises a tank body 11, a heater 12, a collection trough 13, and a delivery member 14. The tank body 11 is connected with the heater 12, the collection trough 13, and the delivery member 14. Through the heater 12, the carbonized paddy in the tank body 11 is heated. The collection trough 13 is configured to collect and store the solid substance separated from the carbonized paddy by means of gas separation. The delivery member 14 is used to deliver the carbonized paddy to the tank body 11 and to deliver the solid substance formed in the tank body 11 to the collection trough 13.

The first condenser 20 is connected with the first water quenching and heating area 10 and configured to condense the gas separated from the carbonized paddy into a liquid. Furthermore, an input end of the first condenser 20 is provided with a filter screen 21. The filter screen 21 is configured to filter impurities and to control the amount of the steam entering the first condenser 20. Moreover, an output end of the first condenser 20 is provided with a gate 22. The gate 22 controls the condensed liquid to be delivered to the second water quenching and heating area 30.

The at least one second water quenching and heating area 30 is connected with the first condenser 20 to receive the liquid which is condensed from the gas by the first condenser 20 and to perform a PH value test. When the PH value of the liquid is alkaline, the liquid is outputted and stored as a pesticide. Preferably, the water quenching device comprises a plurality of second water quenching and heating areas 30. A second condenser 40 is connected between every two of the second water quenching and heating areas 30. When the second water quenching and heating area 30 connected with the first condenser 20 tests and determines that the liquid doesn't reach the alkaline standard, the liquid is heated again by the second water quenching and heating area 30 and changed into a gas. The gas is condensed by the second condenser 40, and the condensed liquid is delivered to the next second water quenching and heating area 30 to give a PH value test. The second water quenching and heating area 30 comprises a tank body 31, a heater 32, and a PH value detector 33. The heater 32 and the PH value detector 33 are disposed in the tank body 31. The PH value detector 33 is electrically connected with the heater 32. When the PH value detector 33 tests the liquid received by the tank body 31 and determines that the liquid doesn't reach the alkaline standard, it will send a signal to the heater 32 and the liquid in the tank body 31 will be heated through the heater 32.

Figure 4:
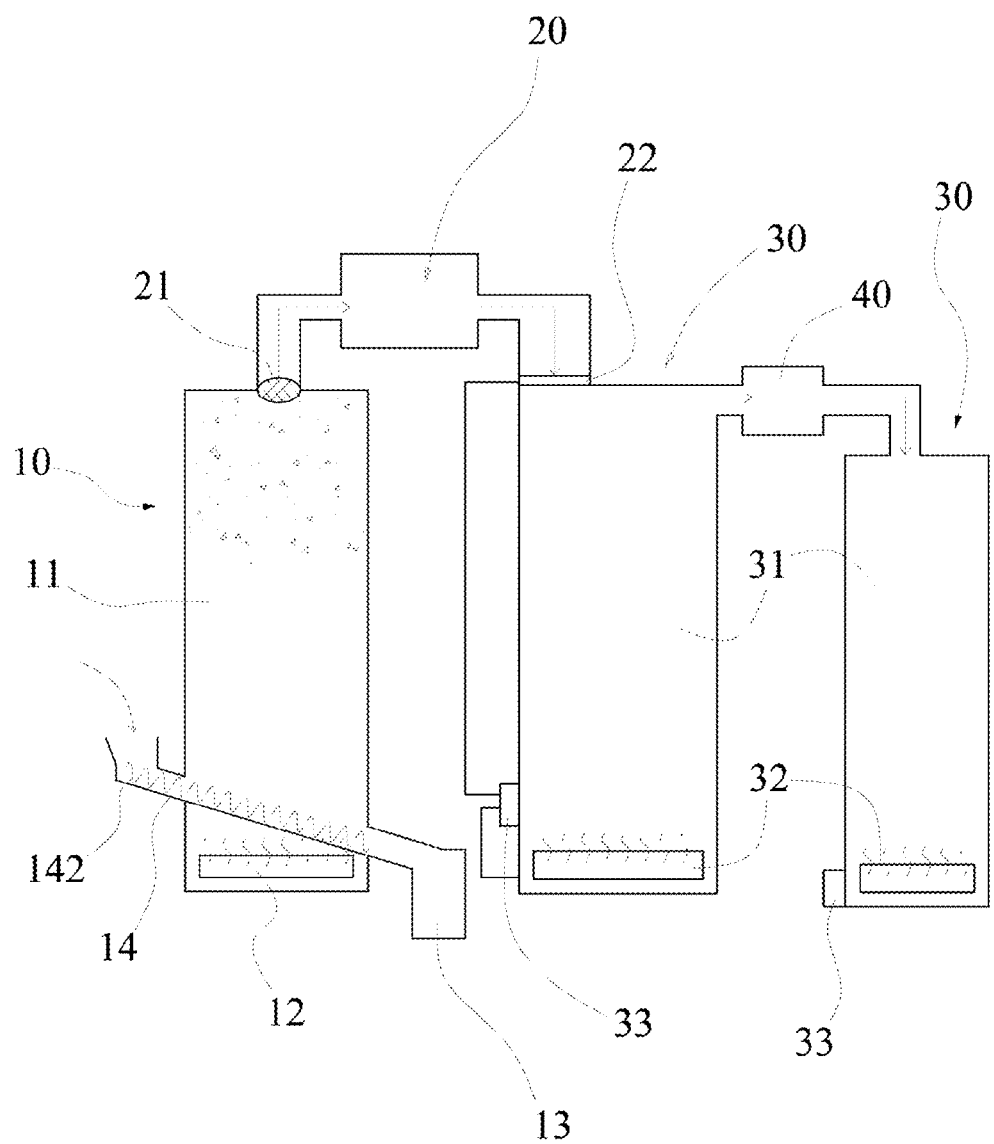
FIG. 4 is another schematic view of a water quenching device for manufacturing a natural pesticide of the present invention.

Furthermore, as shown in FIG. 3, the delivery member 14 has a bevel 141. When the paddy is inputted to the tank body 11, the paddy is slid on the bevel 141 smoothly, enabling the paddy to be delivered to the collection trough 13. In another embodiment, as shown in FIG. 4, the delivery member 14 is provided with a screw rod 142. When the paddy is inputted to the tank body 11, the screw rod 142 can control the speed and the volume of the paddy to be delivered to the tank body 11 so that the paddy can be heated evenly during delivery.

Accordingly, the method and the water quenching device for manufacturing a natural pesticide of the present invention use the carbonized paddy formed by burning paddy as the raw material of the pesticide. Through the procedures of water quenching, heating and condensation, the liquid separated from the carbonized paddy is tested by the PH value detector to determine whether the liquid reaches the alkaline standard or not. If yes, the liquid is outputted as a natural pesticide for use. Even if pests are drug-resistance to increase the dosage of the pesticide, the natural pesticide won't harm the environment and the human health. In addition, the carbonized paddy is quenched and heated to form a solid substance. The solid substance is further heated and crushed to form a small substance. The small substance is added with *trichoderma, actinomyces, bacillus* as a compound organic fertilizer.

Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:
1. A method for manufacturing a natural pesticide, comprising the steps of:
   burning paddy at a high temperature of 400-900° C. into carbonized paddy, wherein the carbonized paddy comprises at least 50% silica, at least 10% organic matter, at least 2% potassium, and at most 2% water;
   using a water quenching device to quench and heat the carbonized paddy, enabling the carbonized paddy to form a gas and a solid substance by means of solid-liquid separation;
   using the water quenching device to condense the gas separated from the carbonized paddy into a liquid; and
   testing a PH value of the liquid after condensation through the water quenching device, wherein when the PH value of the liquid is alkaline, the liquid is outputted and stored as a pesticide;
   wherein the water quenching device comprises:
      a first water quenching and heating area having a tank body and a heater for inputting carbonized paddy, and quenching and heating the carbonized paddy for gas-solid separation to form a gas and a solid substance, wherein the carbonized paddy is formed by burning paddy at a high temperature of 400-900° C. and the carbonized paddy comprises at least 50% silica, at least 10% organic matter, at least 2% potassium, and at most 2% water;
      a first condenser connected with the first water quenching and heating area and configured to condense the gas separated from the carbonized paddy into a liquid; and
      at least one second water quenching and heating area having a tank body and a heater and connected with the first condenser to receive the liquid which is condensed from the gas by the first condenser and to perform a PH value test, wherein when the PH value of the liquid is alkaline, the liquid is outputted and stored as a pesticide,
      wherein the second water quenching and heating area further includes a PH value detector, and the PH value detector is electrically connected with the heater.
2. The method as claimed in claim 1, further comprising the step of:
   using the water quenching device to collect the solid substance separated from the carbonized paddy by means of gas separation, wherein the solid substance is heated and crushed to form a small substance, and the small substance is added with *trichoderma* to form an organic fertilizer.
3. The method as claimed in claim 2, wherein the small substance is added with *actinomyces*.
4. The method as claimed in claim 3, wherein the small substance is added with *bacillus*.
5. A water quenching device for manufacturing a natural pesticide, comprising:
   a first water quenching and heating area having a tank body and a heater for inputting carbonized paddy, and quenching and heating the carbonized paddy for gas-solid separation, to form a gas and a solid substance, wherein the carbonized paddy is formed by burning paddy at a high temperature of 400-900° C. and the carbonized paddy comprises at least 50% silica, at least 10% organic matter, at least 2% potassium, and at most 2% water;
   a first condenser connected with the first water quenching and heating area and configured to condense the gas separated from the carbonized paddy into a liquid; and
   at least one second water quenching and heating area having a tank body and a heater and connected with the first condenser to receive the liquid which is condensed from the gas by the first condenser and to perform a PH value test, wherein when the PH value of the liquid is alkaline, the liquid is outputted and stored as a pesticide,
   wherein the second water quenching and heating area further includes a PH value detector, and the PH value detector is electrically connected with the heater.
6. The water quenching device as claimed in claim 5, wherein the at least one second water quenching and heating area is plural, a second condenser or further condenser is connected between every two of the second water quenching and heating areas, when the second water quenching and heating area connected with the first condenser tests and determines that the liquid doesn't reach an alkaline standard, the liquid is heated again by the second water quenching and heating area and changed into a gas, the gas is condensed by the second condenser, and the liquid after condensation is delivered to the next one of the second water quenching and heating areas to give a PH value test.
7. The water quenching device as claimed in claim 5, wherein the first water quenching and heating area further comprises a collection trough and a delivery member, the collection trough is connected with the tank body for collecting and storing the solid substance separated from the carbonized paddy, the delivery member is connected with the tank body for delivering the carbonized paddy to the tank body and delivering the solid substance formed in the tank body to the collection trough, the delivery member has a bevel.
8. The water quenching device as claimed in claim 7, wherein the first water quenching and heating area further comprises a collection trough and a delivery member, the collection trough is connected with the tank body for collecting and storing the solid substance separated from the carbonized paddy, the delivery member is connected with the tank body for delivering the carbonized paddy to the tank body and delivering the solid substance formed in the tank body to the collection trough, the delivery member is provided with a screw rod.
9. The water quenching device as claimed in claim 7, wherein the solid substance is heated and crushed to form a small substance, and the small substance is added with *trichoderma, actinomyces, bacillus* or a combination thereof to form an organic fertilizer.

10. The water quenching device as claimed in claim 8, wherein the solid substance is heated and crushed to form a small substance, and the small substance is added with *trichoderma, actinomyces, bacillus* or a combination thereof to form an organic fertilizer.

11. The water quenching device as claimed in claim 5, wherein an input end of the first condenser is provided with a filter screen, and an output end of the first condenser is provided with a gate.

\* \* \* \* \*